United States Patent
Komai et al.

(10) Patent No.: US 9,689,789 B2
(45) Date of Patent: Jun. 27, 2017

(54) DAMAGE EVALUATION METHOD AND MAINTENANCE EVALUATION INDEX DECISION METHOD

(75) Inventors: Nobuyoshi Komai, Tokyo (JP); Hiroaki Fukushima, Tokyo (JP); Yuichi Hirakawa, Tokyo (JP); Hiroyuki Ohyama, Tokyo (JP); Takeshi Miyazawa, Tokyo (JP); Hiroaki Yoshida, Tokyo (JP)

(73) Assignee: MITSUBISHI HITACHI POWER SYSTEMS, LTD., Kanagawa (JP)

(*) Notice: Subject to any disclaimer, the term of this patent is extended or adjusted under 35 U.S.C. 154(b) by 453 days.

(21) Appl. No.: 14/241,560

(22) PCT Filed: Sep. 7, 2012

(86) PCT No.: PCT/JP2012/072858
§ 371 (c)(1),
(2), (4) Date: Feb. 27, 2014

(87) PCT Pub. No.: WO2013/038995
PCT Pub. Date: Mar. 21, 2013

(65) Prior Publication Data
US 2015/0019142 A1   Jan. 15, 2015

(30) Foreign Application Priority Data

Sep. 13, 2011 (JP) .................................. 2011-199342

(51) Int. Cl.
*G01B 3/44* (2006.01)
*G01N 17/00* (2006.01)
(Continued)

(52) U.S. Cl.
CPC .............. *G01N 17/00* (2013.01); *G01M 3/00* (2013.01); *G01M 5/0033* (2013.01); *G01N 33/20* (2013.01); *G01N 2203/0296* (2013.01)

(58) Field of Classification Search
CPC ....................................................... G01N 17/00
See application file for complete search history.

(56) References Cited

U.S. PATENT DOCUMENTS

| | | | |
|---|---|---|---|
| 6,810,748 B1 * | 11/2004 | Nishida | G01N 33/20 356/32 |
| 2008/0011091 A1 * | 1/2008 | Weldon | G01L 1/255 73/766 |

FOREIGN PATENT DOCUMENTS

| | | |
|---|---|---|
| CN | 86 1 03018 | 12/1986 |
| CN | 1477383 | 2/2004 |

(Continued)

OTHER PUBLICATIONS

I.J., Perrin, et al "Continuum Damage Mechanics Analyses of Type IV Creep Failure in Ferritic Steel Crossweld Specimens", International Journal of Pressure Vessels and Piping, vol. 76, No. 9, Aug. 31, 1999, pp. 599-617.*

(Continued)

*Primary Examiner* — Aditya Bhat
(74) *Attorney, Agent, or Firm* — Wenderoth, Lind & Ponack, L.L.P.

(57) ABSTRACT

A first measured value of a specific physical quantity at a target portion is correlated with a damage evaluation index to calculate a damage degree corresponding to the first measured value. The specific physical quantity is measured at least once at a position corresponding to the first measurement position in another time period having a different usage elapsed time from that of the first measurement, and these second and subsequent measured values are correlated with damage degrees calculated based on temporal changes corresponding to the second and subsequent measurements. A new damage evaluation index is approximately calculated based on a relationship between the first, second, and (Continued)

subsequent measured values and the damage degrees corresponding to the first, second, and subsequent measured values.

5 Claims, 5 Drawing Sheets

(51) Int. Cl.
  *G01M 5/00* (2006.01)
  *G01M 3/00* (2006.01)
  *G01N 33/20* (2006.01)

(56) References Cited

FOREIGN PATENT DOCUMENTS

| | | |
|---|---|---|
| CN | 1945269 | 4/2007 |
| CN | 101178590 | 5/2008 |
| DE | 43 33 095 | 3/1995 |
| EP | 0 228 014 | 7/1987 |
| JP | 62-177440 | 8/1987 |
| JP | 7-198588 | 8/1995 |
| JP | 07-117531 | 12/1995 |
| JP | 10-170416 | 6/1998 |
| JP | 2000-258306 | 9/2000 |
| JP | 2001-303909 | 10/2001 |
| JP | 2002-340784 | 11/2002 |
| JP | 2003-65914 | 3/2003 |
| JP | 2003-294605 | 10/2003 |
| JP | 2004-44116 | 2/2004 |
| JP | 2004-085347 | 3/2004 |
| JP | 3825378 | 9/2006 |
| JP | 2008-64570 | 3/2008 |
| JP | 2009-92478 | 4/2009 |
| JP | 2009-145185 | 7/2009 |
| JP | 4464043 | 5/2010 |
| JP | 2010-223823 | 10/2010 |
| JP | 4628609 | 2/2011 |
| WO | 01/25743 | 4/2001 |
| WO | 02/14835 | 2/2002 |
| WO | 2010/058209 | 5/2010 |

OTHER PUBLICATIONS

Extended European Search Report issued Apr. 2, 2015 in corresponding European Patent Application No. 12832033.0.
Chinese Office Action issued Apr. 3, 2015 in corresponding Chinese Patent Application No. 201280042319.X with partial English translation.
G. Sposito, et al., "A Review of Non-Destructive Techniques for the Detection of Creep Damage in Power Plant Steels", NDT&E International, vol. 43, No. 7, Oct. 31, 2010, pp. 555-567.
I. J. Perrin, et al., "Continuum Damage Mechanics Analyses of Type IV Creep Failure in Ferritic Steel Crossweld Specimens", International Journal of Pressure Vessels and Piping, vol. 76, No. 9, Aug. 31, 1999, pp. 599-617.
Japanese Office Action issued Sep. 1, 2015 in corresponding Japanese Patent Application No. 2011-199342 with English translation.
Office Action issued Mar. 18, 2016 in corresponding European Application No. 12 832 033.0.
Notice of Allowance issued Mar. 29, 2016 in corresponding Korean Application No. 10-2014-7005471(with English translation).
International Search Report issued Dec. 11, 2012 in International (PCT) Application No. PCT/JP2012/072858 with English translation.
Written Opinion of the International Searching Authority issued Dec. 11, 2012 in International (PCT) Application No. PCT/JP2012/072858 with English translation.

* cited by examiner

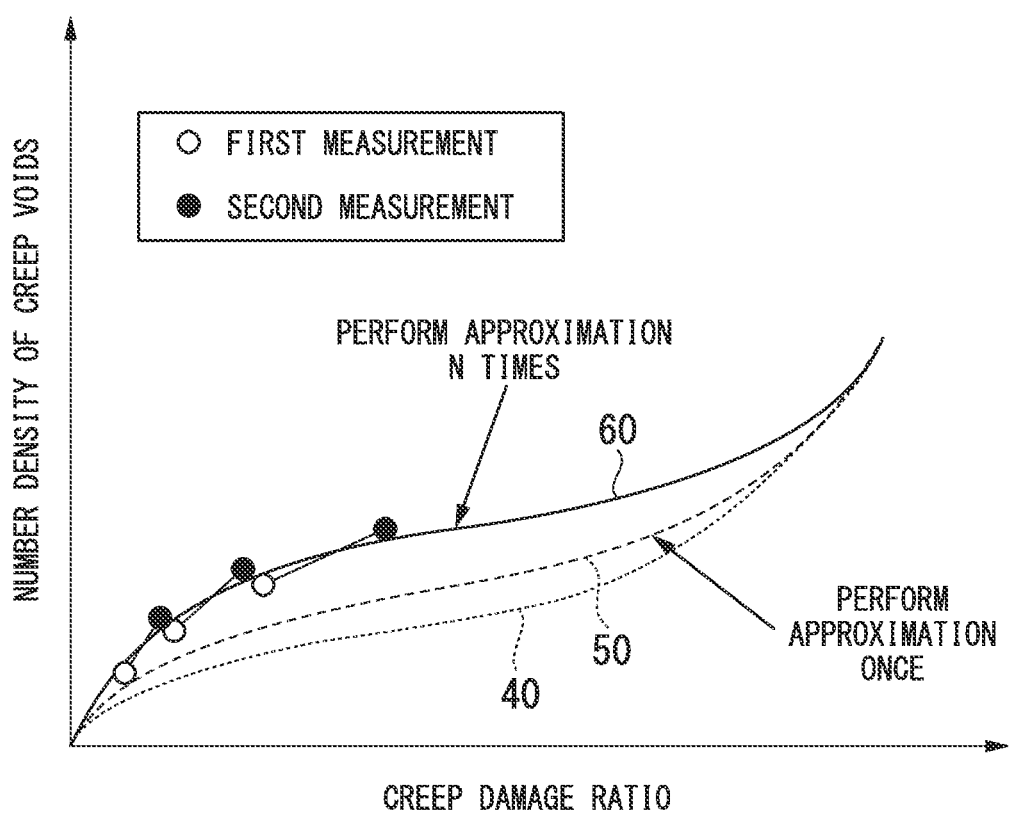

US 9,689,789 B2

DAMAGE EVALUATION METHOD AND MAINTENANCE EVALUATION INDEX DECISION METHOD

TECHNICAL FIELD

The present invention relates to a damage evaluation method capable of evaluating damage such as creep, which occurs in a structural member in a specific usage environment, with higher accuracy; and a maintenance evaluation index decision method using the damage evaluation method.

Priority is claimed on Japanese Patent Application No. 2011-199342, filed Sep. 13, 2011, the content of which is incorporated herein by reference.

BACKGROUND ART

In general, a structural member such as a pipe or a turbine of a thermal power plant is used in a high temperature environment (about 600° C. at a maximum) and is applied with stress. Therefore, after a long-term operation, various kinds of damage such as creep damage unavoidably occur on a target portion of the structural member. Particularly, when creep damage progresses, creep voids and microcracks are generated in a grain boundary of a metal member. Finally, these creep voids and microcracks are connected with each other to generate large cracks, which may lead to breakage.

Therefore, in order to secure the reliability of a structure member, which is used at a high temperature, and to thereby stably operate a power plant or the like, it is important to accurately evaluate the damage of a target portion, to accurately calculate the lifetime, and to perform appropriate maintenance.

As a method of determining damage of a target portion of a structural member, an evaluation method focusing on a specific physical quantity is used. Such an evaluation method includes obtaining a relationship between a damage degree and a specific physical quantity in advance through an experiment, a simulation, or the like; and setting a damage evaluation index for evaluating a damage degree. By correlating this damage evaluation index with a measured value of the specific physical quantity at a target portion, a damage degree thereof is evaluated.

Patent Document 1 discloses a damage degree evaluation method including: measuring a temporal change rate in the number density of creep voids as a specific physical quantity; and correlating this temporal change rate in the number density of creep voids with a damage evaluation index to evaluate a damage degree thereof.

Patent Document 2 discloses a damage degree evaluation method including: measuring a maximum value of an occupancy ratio of creep voids in a grain boundary as a specific physical quantity; and correlating this maximum value of the occupancy ratio of creep voids in the grain boundary with a damage evaluation index to evaluate a damage degree thereof.

RELATED ART DOCUMENT

Patent Document

[Patent Document 1] Japanese Unexamined Patent Application, First Publication No. 2004-85347
[Patent Document 2] PCT International Publication No. WO 2002/014835

SUMMARY OF THE INVENTION

Problems to be Solved by the Invention

In the above-described damage degree evaluation methods, a damage degree is evaluated using the damage evaluation index which is obtained in advance through an experiment, a simulation, or the like. However, depending on actual usage environments, a high stress may be locally applied to a structural member due to stress concentration on a discrete shape portion, or a complex stress field may be formed on the structural member. Therefore, conditions assumed in an experiment or a simulation may be different from actual conditions.

Accordingly, a relationship between a specific physical quantity, which is measured at a target portion of the structural member which is actually used, and a damage degree may be greatly differ from the damage evaluation index which is prepared in advance. As a result, since there are unavoidable errors in a predicted value of damage obtained by the above-described methods, excessive maintenance is performed in consideration of the prediction errors of damage during the maintenance of a plant, industrial equipment, or the like. In this way, since the prediction of heavy damage including errors is required, there is a problem in that the cost required for the maintenance is increased.

Therefore, it is required to reduce cost for maintenance by reducing errors in the prediction of damage and performing minimum examination and maintenance at an optimum time.

An object of the present invention is to provide a damage evaluation method capable of evaluating damage such as creep, which occurs in a structural member of a specific usage environment, with higher accuracy; and a maintenance evaluation index decision method using the damage evaluation method.

Means for Solving the Problems

According to a first aspect of the present invention, a damage evaluation method, which evaluates a damage degree of a target portion which changes over time in a structural member, includes: a first process of correlating a first measured value of a specific physical quantity at the target portion with a damage evaluation index indicating a relationship between the specific physical quantity and a damage degree which is generated based on a temporal change, and calculating a damage degree corresponding to the first measured value; a second process of measuring the specific physical quantity at least once at a position corresponding to the first measurement position in another time period having a different usage elapsed time from that of the first measurement, and correlating these second and subsequent measured values with damage degrees calculated based on temporal changes corresponding to the second and subsequent measurements; and a third process of approximately calculating a new damage evaluation index based on a relationship between the first, second, and subsequent measured values and the damage degrees corresponding to the first, second, and subsequent measured values.

According to the present invention, a first measured value of a specific physical quantity at the target portion is correlated with a damage evaluation index indicating a relationship between the specific physical quantity and a damage degree which is generated based on a temporal change, and calculates a damage degree corresponding to the first measured value. Next, in another time period having a different usage elapsed time from that of the first measurement, the specific physical quantity is measured at least once, and these second and subsequent measured values are correlated with damage degrees calculated based on temporal changes corresponding to the second and subsequent measurements. Next, a new damage evaluation index is approximately calculated based on a relationship between the first, second, and subsequent measured values and the damage degrees. Based on this newly obtained damage evaluation index, a damage degree is evaluated from the measured values of the specific physical quantity.

Since a non-dimensionalized damage degree is used in this damage evaluation index, the first measured value and the second and subsequent measured values measured at different positions can be compared with each other based on the same index indicated by the damage degree. Examples of the damage evaluation index include an evaluation curve that shows the correlation between the specific physical quantity and the damage degree, a numerical table, or media that is electromagnetically stored the numerical data, or the like.

The newly calculated damage evaluation index is approximately obtained based on the measured values of the specific physical quantity which changes according to a temporal change of a target portion applied with a stress in an actual usage environment at a usage temperature. Therefore, the accuracy of the new damage evaluation index can be improved as compared to the initial damage evaluation index determined through an experiment or a simulation. Based on the newly obtained damage evaluation index, the damage degree can be evaluated from the measured values of the specific physical quantity, and the damage degree of a target portion of a structure can be evaluated with high accuracy.

According to a second aspect of the present invention, in the damage evaluation method according to the first aspect, the first process, the second process, and the third process are repeated based on the new damage evaluation index.

By repeating the first process, the second process, and the third process, a difference between the damage evaluation index and the correlation of the measured values of the specific physical quantity and the damage degree can be decreased. Based on the new damage evaluation index, the damage degree can be evaluated from the measured values of the specific physical quantity, and the damage degree can be evaluated with high accuracy.

According to a third aspect of the present invention, in the damage evaluation method according to the first or second aspect, a damage evaluation curve is used as the damage evaluation index.

The damage evaluation curve is a curve representing the relationship between the specific physical quantity and the damage degree, in which the relationship between the specific physical quantity and the damage degree is continuously represented. In the damage evaluation curve, since the specific physical quantity and the damage degree which change over time are continuously represented, the relationship between the specific physical quantity and the damage degree is visually easily understood.

In addition, by using the damage evaluation curve, the damage degree can be easily evaluated using the measured values of the specific physical quantity.

According to a fourth embodiment of the present invention, in the damage evaluation method according to any one of the first to third embodiments, the damage degree is a creep damage ratio.

The creep damage ratio is the degree of damage which occurs due to the creep of a structural member used in a high-temperature environment. By using the creep damage ratio as the damage degree, the creep damage ratio can be easily determined from the measured values of the specific physical quantity.

According to a fifth aspect of the present invention, in the damage evaluation method according to the fourth aspect, the specific physical quantity is a number density of creep voids. That is, the specific physical quantity is the number of creep voids per unit area.

By using the number density of creep voids as the specific physical quantity, the physical quantity can be easily measured, and the creep damage ratio can be effectively evaluated.

According to a sixth aspect of the present invention, in the damage evaluation method according to any one of the first to fifth aspects, the structural member is formed of heat-resistant steel.

The heat-resistant steel is used as a structural member which is used in a high-temperature and high-pressure environment, for example, a pipe of a thermal power plant boiler. By applying the damage evaluation method to heat-resistant steel which is used in a strict usage environment and is difficult to evaluate, the damage degree of the heat-resistant steel can be evaluated with high accuracy.

According to a seventh aspect of the present invention, in the damage evaluation method according to the sixth aspect, the target portion is a welding heat-affected portion of the structural member formed of heat-resistant steel.

In the welding heat-affected portion of the heat-resistant steel, a structure thereof is changed or recovered by reverse transformation due to the effect of welding heat input, and metallographic structures before and after being affected by the heat are different from each other. Therefore, as compared to portions which are not affected by the welding heat, the creep strength is weakened, creep deformation is concentrated to increase a multiaxial degree, and thus creep voids are likely to be formed. Accordingly, creep damage more easily occur as compared to the other portions. By using the welding heat-affected portion of the heat-resistant steel as the measurement position of the specific physical quantity, the damage of the welding heat-affected portion of the heat-resistant steel can be evaluated from the measured values of the specific physical quantity with high accuracy.

According to an aspect of the present invention, a maintenance evaluation index decision method is established using the damage evaluation method according to any one of the first to seventh aspects.

The maintenance evaluation index is an evaluation index which indicates the correlation of the specific physical quantity at the target portion of the structural member with the damage degree and is used for evaluating the damage degree of the target portion of the structural member during maintenance.

The maintenance evaluation index is obtained as follows. By using a first measured value of the specific physical quantity and a damage evaluation index indicating a relationship between the specific physical quantity and a damage degree, which is generated based on a temporal change, a damage degree corresponding to the first measured value is calculated. Next, in another time period having a different usage elapsed time from that of the first measurement, the specific physical quantity is measured at least once, and these second and subsequent measured values are correlated with damage degrees calculated based on temporal changes corresponding to the second and subsequent measurements.

Next, a new damage evaluation index is approximately calculated based on a relationship between the first, second, and subsequent measured values and the damage degrees.

By obtaining the new damage evaluation index as described above, it is possible to obtain the maintenance evaluation index which is applicable to maintenance with higher accuracy. Based on this maintenance evaluation index, the damage degree can be effectively and easily evaluated from the measured values of the specific physical quantity with high accuracy according to various circumstances. As a result, maintenance can be appropriately performed.

Effect of the Invention

With the damage evaluation method and the maintenance evaluation index decision method according to the present invention, damage such as creep, which occurs in a structural member of a specific usage environment, can be evaluated with higher accuracy.

BRIEF DESCRIPTION OF DRAWINGS

FIG. 7 is a diagram illustrating a damage evaluation method in which the first process, the second process, and the third process are repeated.

DESCRIPTION OF EMBODIMENTS

Hereinafter, embodiments of the present invention will be described with reference to the drawings.

In this embodiment, an example in which a damage evaluation method is applied to a welding heat-affected portion (target portion) of a pipe of heat-resistant steel such as a boiler, which is used in a high-temperature and high-pressure environment, to evaluate a creep damage degree will be described.

Figure 1:
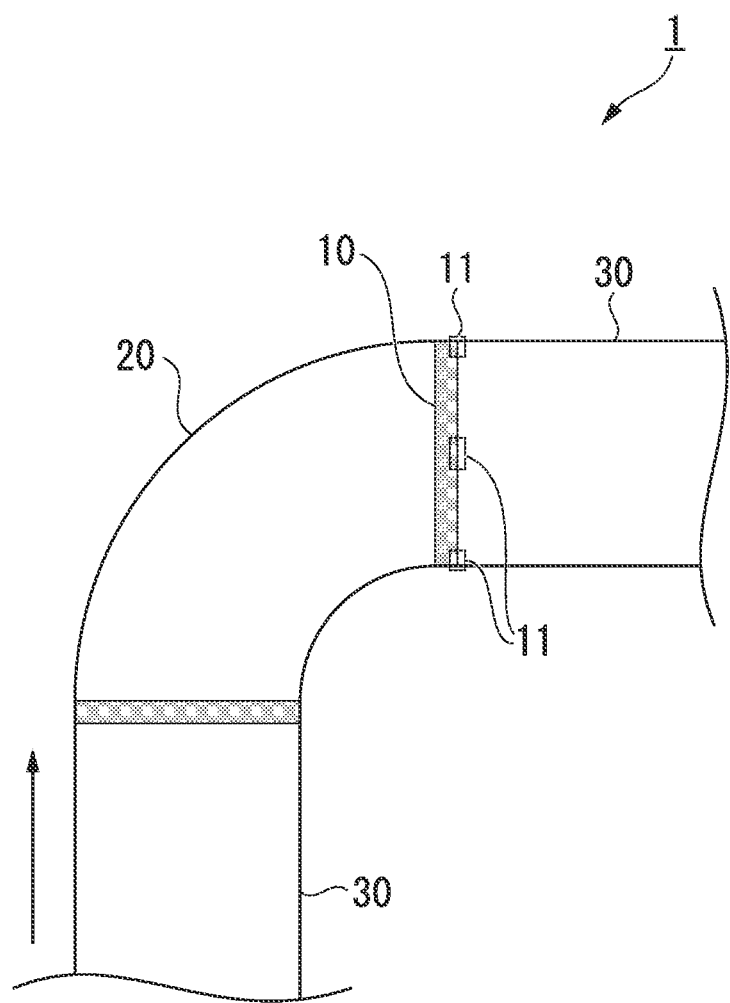
FIG. 1 is a diagram schematically illustrating a pipe and a welding heat-affected portion (target portion) of a boiler to which a creep damage evaluation method according to an embodiment of the present invention is applied.

FIG. 1 illustrates a pipe 1 of a boiler which is an evaluation target of the damage evaluation method according to this embodiment.

Through the inside of the pipe 1, high-temperature vapor flows in a direction indicated by an arrow of FIG. 1. A weld joint portion 10 of the pipe 1 is a joint through which a bent portion 20 and a linear portion 30, which are formed of heat-resistant steel, are welded together.

In the weld joint portion 10, the number density of creep voids is measured at a welding heat-affected portion 11 (target portion) adjacent to the weld joint portion 10 in order to evaluate a creep damage ratio. The number density of creep voids can be obtained by measuring creep voids using, for example, a replica method and obtaining the number of creep voids per predetermined area. The replica method includes performing a predetermined treatment on the surface of the welding heat-affected portion 11 to make a metallographic structure appear; transferring convex and concave shapes of the metallographic structure onto a film; and observing the transferred convex and concave shapes using an optical microscope, a scanning electron microscope, or the like.

In this example of the embodiment, the creep damage ratio is evaluated from the number density of creep voids which is measured at the welding heat-affected portion 11 provided on the weld joint portion 10.

The creep damage ratio is calculated from the following expression.

$$\text{Creep Damage Ratio} = (\text{Usage Elapsed Time})/\{(\text{Usage Elapsed Time}) + (\text{Remaining Lifetime of Structural Member})\}$$

The usage elapsed time refers to a total time for which a structural member is used in a specific usage environment. The remaining lifetime of a structural member refers to the remaining time until the structural member which is used in a specific environment is broken. The sum of the usage elapsed time and the remaining lifetime of a structural member is the time which is required for the structural member to be broken after the usage in a specific environment, and this sum is called the total lifetime.

Heat-resistant steel to be used is appropriately selected according to the usage temperature and applied stress of a pipe or a structural member. Examples of a representative material to be used include 2 Cr steel; and 9 Cr steel and 12 Cr steel which are known as high-strength ferritic steel. In a portion requiring higher corrosion resistance and creep strength, other ferritic steels, austenitic steels, Fe-based alloys, Ni-based alloys, and the like may be used.

Hereinafter, the order of the creep damage evaluation method according to this embodiment will be described.

Figure 2:
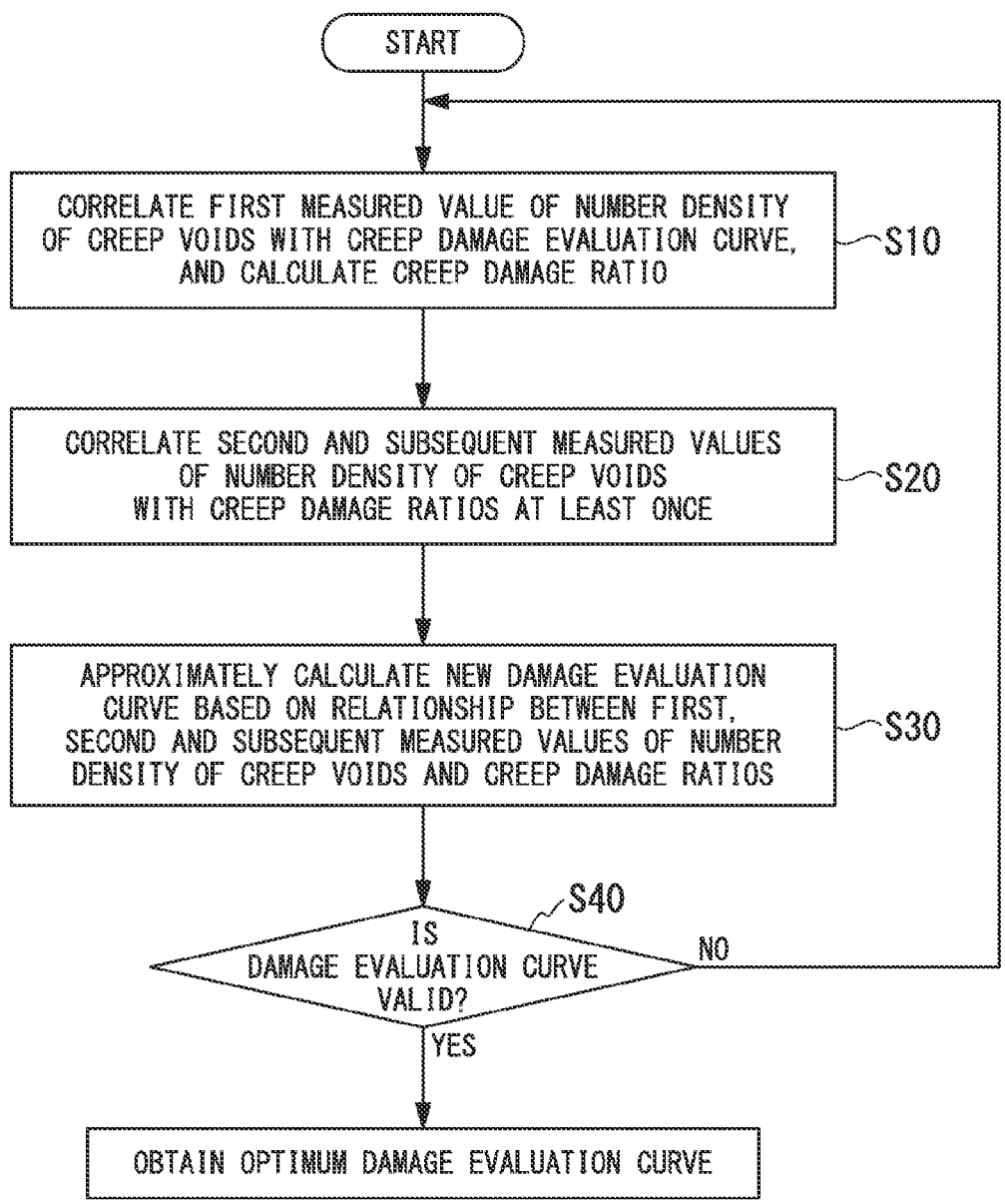
FIG. 2 is a flowchart schematically illustrating the order of the creep damage evaluation method according to the embodiment.

The creep damage evaluation method according to this embodiment is performed according to the order of a flowchart illustrated in FIG. 2. That is, an optimum creep damage evaluation curve is obtained by decreasing a difference between a relationship of the damage ratio corresponding to the number density of creep voids and the damage evaluation index. Using this optimum creep damage evaluation curve, the creep damage ratio is determined.

The order for obtaining the creep damage evaluation curve includes, for example, a first process S10, a second process S20, a third process S30, and a determination process S40. In the determination process S40, the validity of the creep damage evaluation curve is determined.

(First Process S10)

The first process S10 is a process of calculating the creep damage ratio from the number density of creep voids. A method of calculating the creep damage ratio will be described below.

Figure 3:
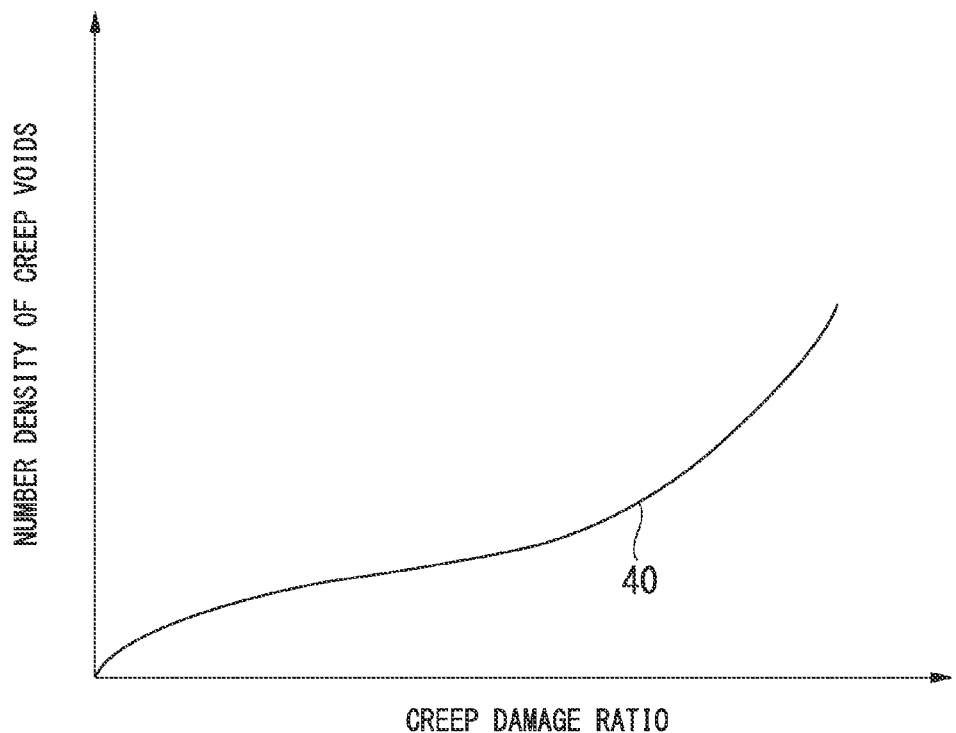
FIG. 3 is a diagram illustrating a creep damage evaluation curve according to the embodiment.

FIG. 3 illustrates a creep damage evaluation curve 40 representing a relationship between the number density of creep voids at a welding heat-affected portion of heat-resistant steel, which is used in a high-temperature environment, and the creep damage ratio. This creep damage evaluation curve 40 is obtained in advance, for example, through a laboratory experiment or using cumulative data or the like in a database.

A first measurement of the number density of creep voids is performed at the welding heat-affected portion 11 of the pipe 1 which is actually used. It is preferable that the number of the measurement positions at this time be one or more.

The first measured value of the number density of creep voids is correlated with the creep damage evaluation curve 40 of FIG. 3 to calculate a creep damage ratio.

Figure 4:
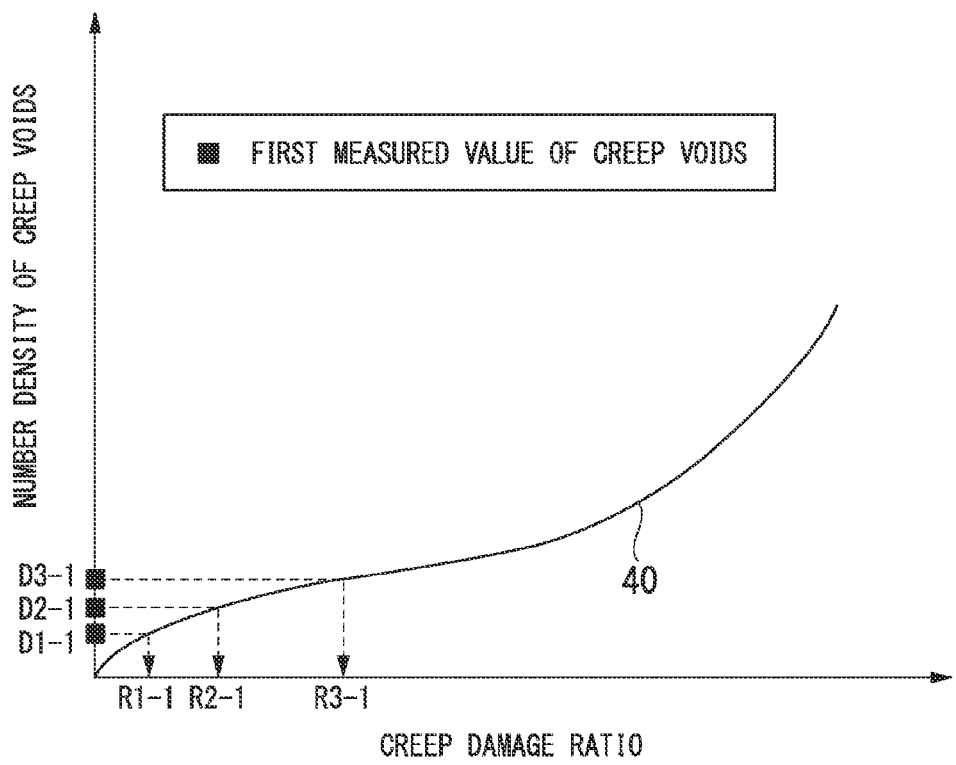
FIG. 4 is a diagram illustrating a first process of the creep damage evaluation method according to the embodiment.

Specifically, when the number of the first measurement positions of creep voids is three, measured values D1-1, D2-1, and D3-1 at the respective measurement positions are plotted as illustrated in FIG. 4, and creep damage ratios R1-1, R2-1, and R3-1 corresponding to the measured values D1-1, D2-1, and D3-1 of the creep damage evaluation curve 40 are calculated. Next, using the creep damage ratios and the usage elapsed time, the total lifetime of the welding heat-affected portion 11 at each measurement position is calculated.

(Second Process S20)

The second process S20 is a process of correlating second and subsequent measured values of the number density of creep voids with creep damage ratios.

In another time period having a different usage elapsed time from that of the first measurement, second and subsequent measurements of the number density of creep voids are preformed at least once at the welding heat-affected portion 11 of the pipe 1. The measurement positions at this time are positions corresponding to the first measurement positions.

The positions corresponding to the first measurement positions refer to, for example, the same positions as the first measurement positions or the positions of which the damage degrees are the same as those of the first measurement positions.

Figure 5:
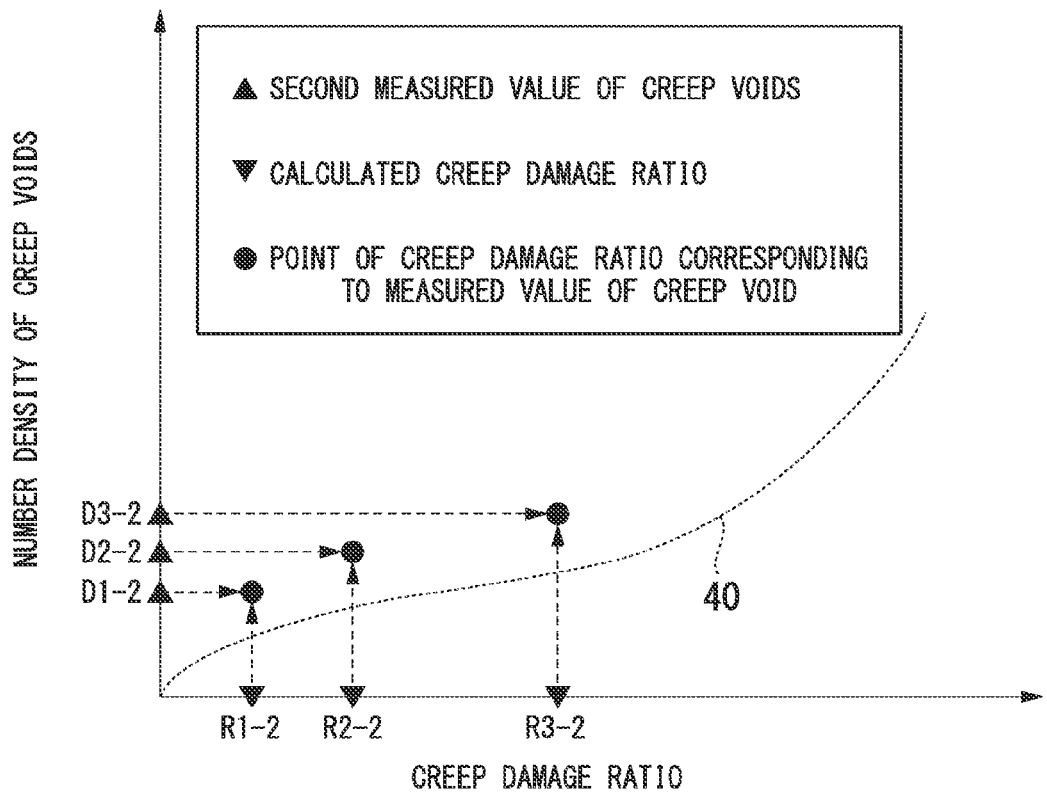
FIG. 5 is a diagram illustrating a second process of the creep damage evaluation method according to the embodiment.

In this embodiment, as illustrated in FIG. 5, the creep damage ratio at each measurement point is calculated using the usage elapsed time and the number density of creep voids in the second measurement and the total lifetime calculated in the first process.

Next, as illustrated in FIG. 5, the measured values (D1-2, D2-2, D3-2) of the number density of creep voids in the second measurement are correlated with the creep damage ratios (R1-2, R2-2, R3-2) calculated from the above-described second and subsequent measured values of the number density of creep voids.

FIG. 5 illustrates a case where the second measurement is performed at three positions in the same manner as that of the first measurement, and the three measured values of the number density of creep voids are correlated with the creep damage ratios once. In the second process, the number density of creep voids may be measured at least once, and three and subsequent measurements may be performed.

(Third Process S30)

The third process S30 is a process of calculating a new creep damage evaluation curve.

Figure 6:
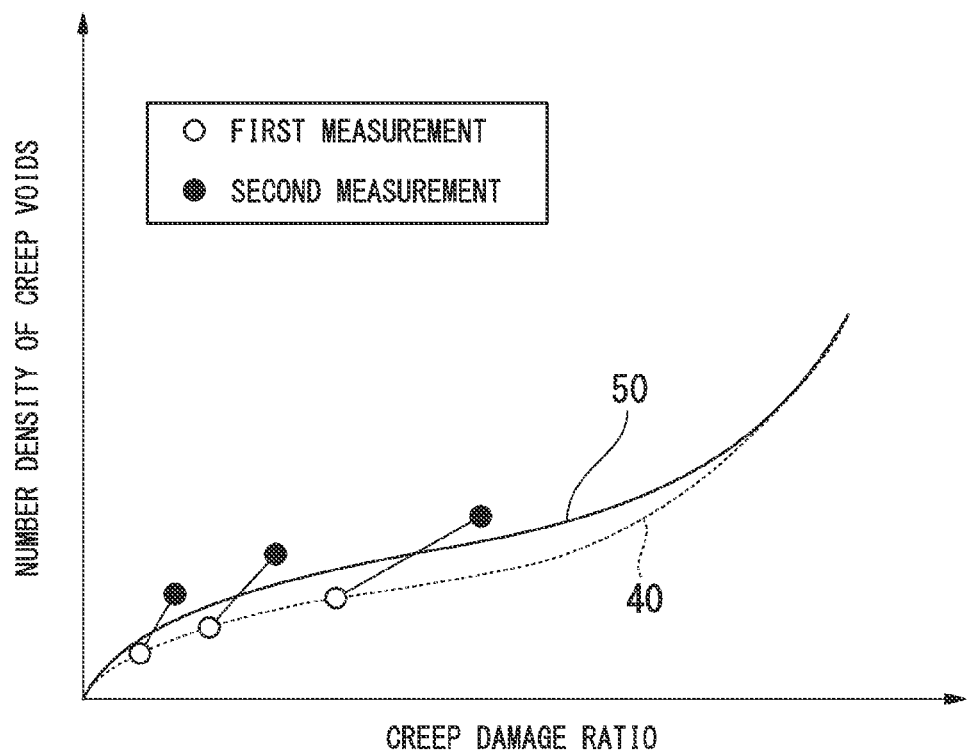
FIG. 6 is a diagram illustrating a third process of the creep damage evaluation method according to the embodiment.

As illustrated in FIG. 6, a new creep damage evaluation curve 50 is approximately calculated based on a relationship between the first, second, and subsequent measured values of the number density of creep voids and the damage creep ratios corresponding to the above measured values.

In order to approximately calculate the new creep damage evaluation curve 50 based on the measurement data, for example, regression analysis may be used. Specifically, the approximation may be performed by log approximation, polynomial approximation, a least-square method, or the like.

In the creep damage evaluation curve 50 of FIG. 6, the first and second measured values of the number density of creep voids are plotted. A slight difference between the damage evaluation curve 50 and the measured values of the number density of creep voids can be confirmed.

(Determination Process S40)

The determination process S40 is a process of determining whether or not the new creep damage evaluation curve 50 obtained in the third process S30 is valid.

For example, when the new creep damage evaluation curve 50 and the relationship between the measured values of the number density of creep voids and the creep damage ratios are out of a predetermined range, it is preferable that the first process, the second process, and the third process be further performed using the new creep damage evaluation curve 50. These processes are repeated until the obtained creep damage evaluation curve and the relationship between the first and second measured values of the number density of creep voids and the creep damage ratios are within the desired predetermined range. Then, as illustrated in FIG. 7, a creep damage evaluation curve 60 where a difference from the measured values is small is obtained (in FIG. 7, the creep damage evaluation curve 60 obtained after performing the first process, the second process, and the third process N times is illustrated).

In this example, the creep damage evaluation curve 60 matches well with the relationship between the first and second measured values of the number density of creep voids and the creep damage ratios.

When the new creep damage evaluation curve and the relationship between the first and second measured values of the number density of creep voids and the creep damage ratios are within the predetermined range, it is evaluated that an optimum damage evaluation curve is obtained.

Regarding the determination of whether or not the creep damage evaluation curve is valid, for example, when differences between the creep damage ratios, which are calculated from the measured values of the number density of creep voids, and damage ratios of the creep damage evaluation curve are less than a predetermined ratio (for example, 5%), it is determined that an optimum damage evaluation curve is obtained. It is preferable that whether or not the creep damage evaluation curve is valid be comprehensively determined based on, for example, a past database or a safety factor of a welding heat-affected portion (target portion) of a structural member.

In the creep damage evaluation method according to this embodiment, a high-accuracy new creep damage evaluation curve is obtained through the first process S10, the second process S20, and the third process S30. Since a non-dimensionalized creep damage degree is used in this creep damage evaluation index, the first measured value and the second and subsequent measured values measured at different positions can be compared with each other based on the same index indicated by the damage degree.

In the determination process S40, whether or not the creep damage evaluation curve is valid can be determined. When it is determined that a creep damage evaluation curve is valid, this creep damage evaluation curve is set as the optimum creep evaluation curve.

When it is determined that a creep damage evaluation curve is not valid, the first process, the second process, and the third process are repeated based on the newly obtained creep damage evaluation curve until it is determined that the newly obtained creep evaluation curve is valid. As a result, the optimum creep damage evaluation curve is obtained, and the accuracy can be further increased.

Based on the creep damage evaluation curve obtained as above, the creep damage ratio can be evaluated from the measured values of the number density of creep voids with higher accuracy. As a result, the remaining lifetime can be accurately determined even in a portion, such as a welding heat-affected portion of heat-resistant steel, where creep damage is likely to occur. As a result, maintenance can be performed at an appropriate time, and the cost required for the maintenance of equipment can be reduced.

In this embodiment, since the creep damage evaluation curve is used, the relationship between the number density of creep voids and the creep damage ratio is visually easily understood. The creep damage ratio can be easily and effectively determined from the creep damage evaluation curve and the measured values of the number density of creep voids.

Hereinabove, the creep damage evaluation method, which is the embodiment of the present invention, of a welding heat-affected portion of a pipe of a boiler or the like has been described, but the present invention is not limited thereto. The present invention can be appropriately modified within a range not departing from the technical scope of the present invention.

In the above-described embodiment, the method of evaluating a creep damage ratio has been described. However, the present invention may be applied to cases where the degree of damage, which occurs due to a temporal change, of a target portion of a structural member is evaluated, for example, where the degree of fatigue, abrasion, or corrosion of the structural member is evaluated.

In the above-described embodiment, the number density of creep voids is used as the specific physical quantity. However, other specific physical quantities can be measured as long as they are specific physical quantities which change over time according to the damage degree of a target portion, for example, the hardness and elongation of a target portion, the number of creep voids and change rate at a specific portion of crystal grains, or the defect property of the inside of a sheet which can be detected through a ultrasonic inspection or a radiological inspection.

In the above-described embodiment, the case where the damage evaluation curve is used has been described, but the present invention is not limited to the evaluation curve. A numerical table that shows the correlation between the specific physical quantity and the damage degree or media that is electromagnetically stored the numerical data may be used.

In the above-described embodiment, the case where the pipe 1 is formed of heat-resistant steel has been described. However, the structural member is formed of any material as long as it has a target portion which is damaged according to a temporal change.

In the above-described embodiment, the position at which the number density of creep voids is measured is a welding heat-affected portion of a pipe. However, a position which is damaged according to a temporal change, for example, a blade groove portion of a turbine or a base material portion of a heat-transfer pipe and a pipe may be measured.

In the above-described embodiment, in the first process, the total lifetime of a welding heat-affected portion (target portion) is calculated, but the remaining lifetime thereof may be calculated.

DESCRIPTION OF REFERENCE NUMERALS

10 WELD JOINT PORTION
11 WELDING HEAT-AFFECTED PORTION (TARGET PORTION)
40, 50, 60 CREEP DAMAGE EVALUATION CURVE (DAMAGE EVALUATION INDEX)

The invention claimed is:

1. A damage evaluation method, which evaluates a creep damage ratio of a target portion which changes over time in a structural member, the damage evaluation method comprising:
a first process of correlating a first measured value of a number density of creep voids at a first measurement position of the target portion with a damage evaluation curve indicating a relationship between a number density of the creep voids and a creep damage ratio which is generated based on a temporal change, and calculating a creep damage ratio corresponding to the first measured value;
a second process of measuring a measured value of the number density of the creep voids at least once, as a second measured value, at a position corresponding to the first measurement position in another time period having a different usage elapsed time from that of the first measured value, and correlating the second and any subsequent measured values with a creep damage ratio calculated based on temporal changes corresponding to the second and any subsequent measured values;
a third process of approximately calculating a new damage evaluation curve based on a relationship between the first, second, and any subsequent measured values and the creep damage ratio corresponding to the first, second, and any subsequent measured values;
a fourth process of evaluating the creep damage ratio from the first, second, and any subsequent measured values of the number density of the creep voids, based on the new damage evaluation curve calculated in the third process; and
a fifth process of determining a lifetime of the structural member based on the fourth process of evaluating the creep damage ratio for performing maintenance on the structural member when appropriate based on the fourth process of evaluating the creep damage ratio.

2. The damage evaluation method according to claim 1, wherein the first process, the second process, and the third process are repeated based on the new damage evaluation curve.

3. The damage evaluation method according to claim 1, wherein the structural member is formed of heat-resistant steel.

4. The damage evaluation method according to claim 3, wherein the target portion is a welding heat-affected portion of the structural member formed of heat-resistant steel.

5. A maintenance evaluation index decision method using the damage evaluation method according to claim 1.

* * * * *